United States Patent [19]

Lee

[11] Patent Number: 5,292,332
[45] Date of Patent: Mar. 8, 1994

[54] METHODS AND DEVICE FOR PERCUTANCEOUS SEALING OF ARTERIAL PUNCTURE SITES

[76] Inventor: Benjamin I. Lee, 4911 Van Ness St, NW., Washington, D.C. 20016

[21] Appl. No.: 918,614

[22] Filed: Jul. 27, 1992

[51] Int. Cl.$^5$ .............................. A61B 17/00
[52] U.S. Cl. ..................... 606/213; 606/215
[58] Field of Search .................. 606/213, 215, 232

[56] References Cited

U.S. PATENT DOCUMENTS

| | | | |
|---|---|---|---|
| 4,738,255 | 4/1988 | Goble et al. | 606/232 |
| 4,744,364 | 5/1988 | Kensey | 606/213 |
| 4,852,568 | 8/1989 | Kensey | 606/213 |
| 4,890,612 | 1/1990 | Kensey | 606/213 |
| 5,021,059 | 6/1991 | Kensey et al. | 606/213 |
| 5,053,096 | 10/1991 | Janese | 606/215 |
| 5,061,274 | 10/1991 | Kensey et al. | 606/215 |
| 5,108,421 | 4/1992 | Fowler | 606/215 |
| 5,123,914 | 6/1992 | Cope | 606/215 |

FOREIGN PATENT DOCUMENTS

0476178A1  3/1992  European Pat. Off. .

Primary Examiner—Peter A. Aschenbrenner
Assistant Examiner—Gary Jackson
Attorney, Agent, or Firm—Cushman, Darby & Cushman

[57] ABSTRACT

A method is provided for closing a puncture in a wall of an artery made for the purpose of moving an elongated catheter into the artery in which an exterior guide tube is extended through the adjacent skin area through the body containing the artery, through the puncture in the wall of the artery and into the artery so as to enable the catheter to be guidingly moved through the guide tube and into the artery. The method includes the steps of withdrawing the catheter from the guide tube, extending a plug having a removable guide wire extending longitudinally therethrough into the guide tube so that the guide wire extends from the plug through the puncture, moving the guide tube outwardly so that it no longer extends within the puncture and leaves the guide wire extending through the puncture, moving the plug inwardly along the guide wire into blocking relation with the puncture, and withdrawing the guide wire from the plug so as to leave the plug sealed in blocking relation with the puncture. A device is also provided to employ the method.

43 Claims, 7 Drawing Sheets

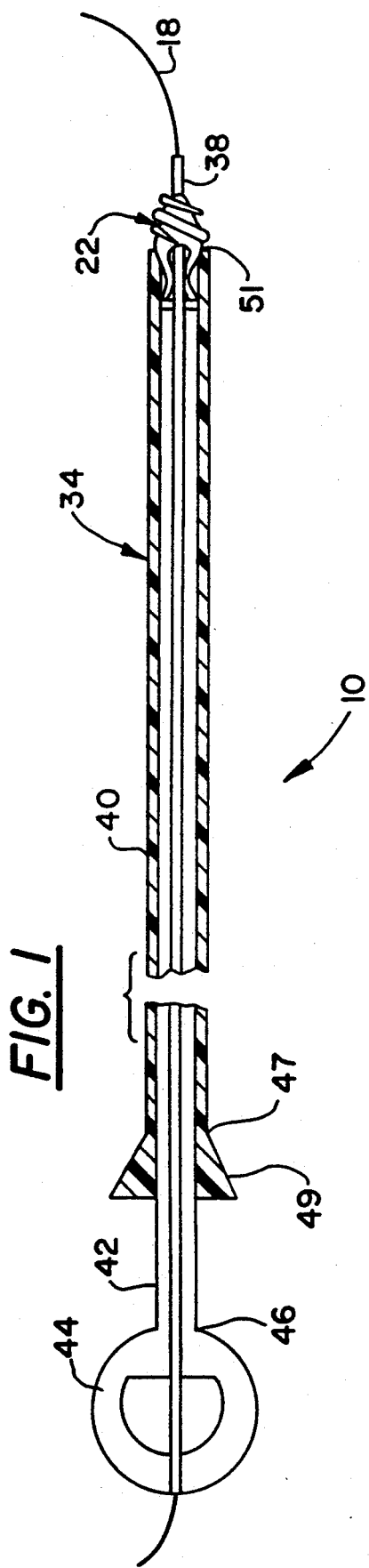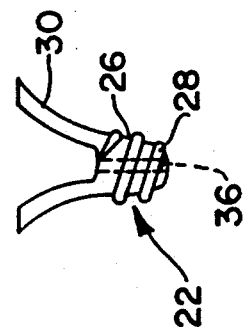

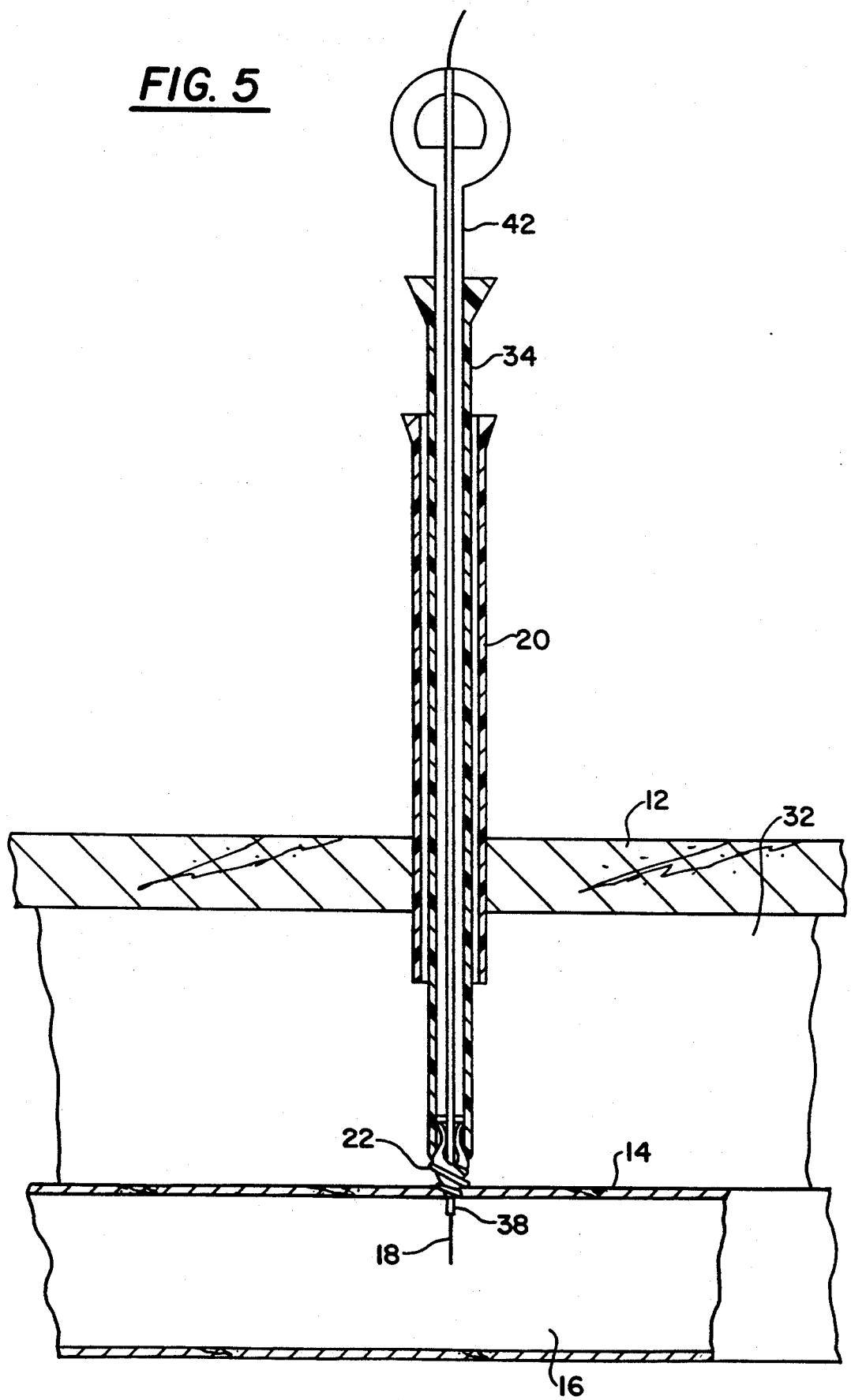

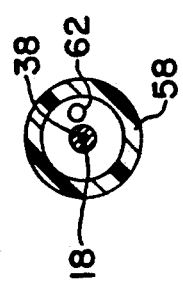
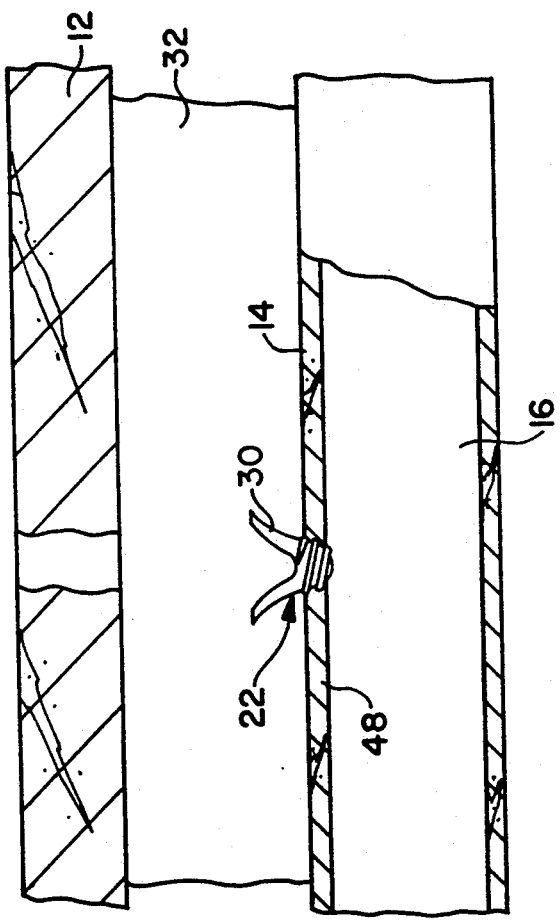
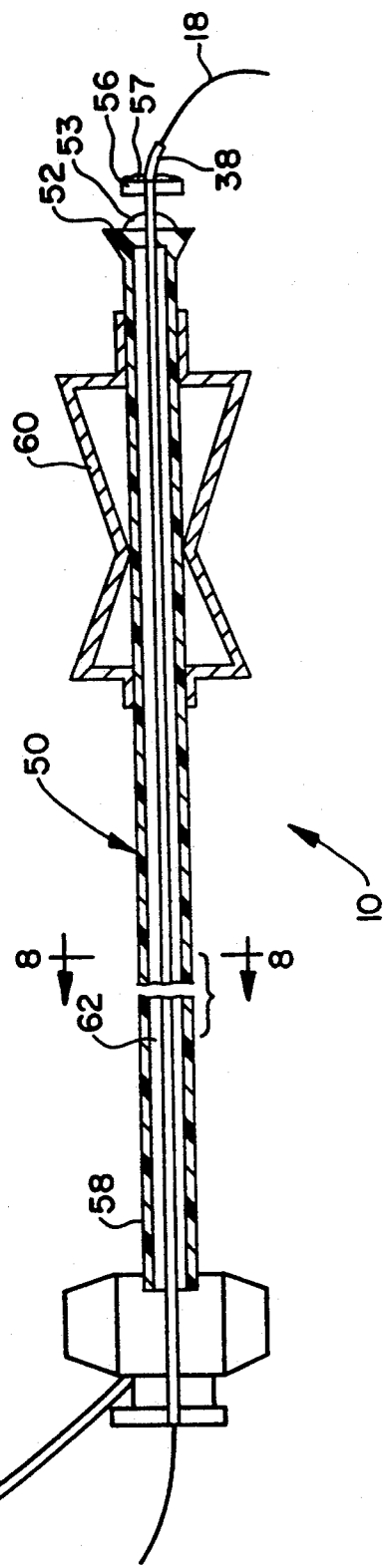
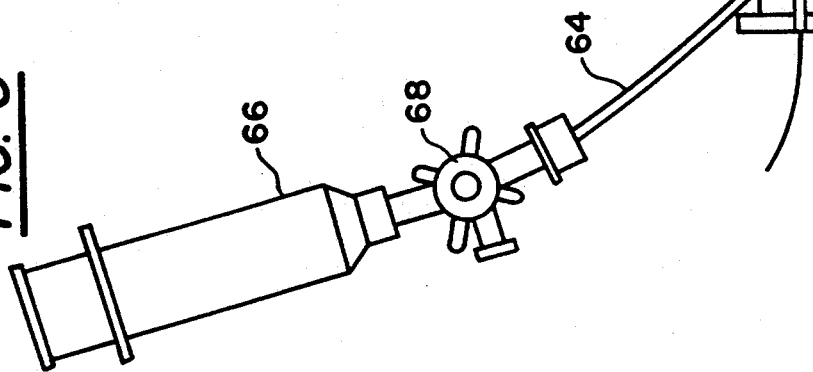

METHODS AND DEVICE FOR PERCUTANCEOUS SEALING OF ARTERIAL PUNCTURE SITES

BACKGROUND OF THE INVENTION

1. Field of the Invention

This invention relates to medical devices and more particularly to a method for percutaneously sealing a puncture in an artery without the need for prolonged manual pressure and without impeding blood flow within the lumen of the artery. A device is also provided to employ the sealing method.

2. Description of the Related Art

Many therapeutic procedures, especially those pertaining to the treatment of atherosclerotic coronary artery and peripheral vascular disease involve percutaneous entry into blood vessels using catheters, guide wires and other devices passed through vascular sheaths. Once the procedure is terminated and the catheters and sheaths removed, adequate hemostasis usually requires direct manual pressure over the arterial puncture site for a duration of 20 to 40 minutes, following which, the patient must remain immobile for an additional 2 to 6 hours. Patient motion during this time and/or inadequate hemostasis may result in serious bleeding complications such as hematoma or pseudoaneurysm formation, which may require surgical repair.

With the increasing utilization of outpatient catheterization procedures, aggressive anticoagulation regimens and larger intraluminal devices, an effective, simple and rapid method of arterial puncture site hemostasis would decrease hospital costs by the more efficient utilization of health care personnel and by shortening the length of hospital stay.

Conventional devices have been developed to close a puncture in a blood vessel, duct or lumen without the need to apply prolonged, direct manual pressure thereto. For example, U.S. Pat. Nos. 4,852,568; 4,890,612; and 4,744,364 to Kensey disclose hemostatic plug devices which are inserted through an arterial sheath into the lumen of the artery prior to removal of the sheath. These plug devices are then pulled back into the arterial puncture site by an attached suture to occlude the puncture site as the arterial sheath is removed. The plug devices are made of bio-absorbable material and have an enlarged head portion which, when pulled back, seals the luminal surface of the puncture site. However, such devices present numerous disadvantages. For example, it is difficult to advance the device into atherosclerotic arteries and locate the puncture site to effectively dispose the plug therein, without the use of a guide wire. There is also a potential for the intraluminal head portion of the device to occlude blood flow or cause thrombosis in vessels whose luminal diameter is severely narrowed. Finally, there is a potential for the intraluminal portion of the device to embolize distally as it is bio-degraded.

European Patent Application No. 476,178A1 discloses a device for placing styptic material on perforated blood vessels. The device uses a guide wire to locate the puncture site. A dilator is pushed along the guide wire. A tube is guided along the dilator to the puncture site. The dilator and guide wire are then removed from the tube. A plug is then pushed through the tube to block the puncture site. However, since the guide wire is removed prior to inserting the plug, it cannot be assured that the plug is in a position so as to properly block the puncture site.

A need therefore exists to provide a method for closing a puncture in a lumen which utilizes a guide wire for disposing a plug in blocking relation with the puncture. A need exists to assure the plug does not occlude blood flow in vessels of narrow luminal diameters.

SUMMARY OF THE INVENTION

An object of the present invention is to fulfill the need referred to above. In accordance with the principles of the present invention, this objective is obtained by providing a method for closing a puncture in a wall of an artery made for the purpose of moving an elongated catheter into the artery in which an exterior guide tube is extended through the adjacent skin area through the body containing the artery, through the puncture in the wall of the artery and into the artery so as to enable the catheter to be guidingly moved through the guide tube and into the artery. The method includes the steps of withdrawing the catheter from the guide tube, extending a plug having a removable guide wire extending longitudinally therethrough into the guide tube so that the guide wire extends from the plug through the puncture, moving the guide tube outwardly so that it no longer extends within the puncture and leaves the guide wire extending through the puncture, moving the plug inwardly along the guide wire into blocking relation with the puncture, and withdrawing the guide wire from the plug so as to leave the plug sealed in blocking relation with the puncture.

In accordance with a further aspect of the invention a hemostatic device is provided to deliver a plug to the vessel puncture. In accordance with the principles of the present invention, this object is achieved by providing a device for closing a puncture in a wall of an artery. The device includes an elongated member having a distal end, the elongated member is sized to be fitted through an incision so that the distal end is disposed near the puncture in the artery, a plug member for plugging the puncture being disposed at the distal end of the elongated member, movable guide means extending longitudinally through the plug member and through the puncture for guiding the plug member to the puncture, and means for ejecting the plug member from the distal end of the elongated member so as to place the plug member in blocking relation with the puncture. A portion of the plug member engages a wall of the artery when disposed in the blocking relation, so as to seal the puncture.

These and other objects of the present invention will become apparent during the course of the following detailed description and appended claims.

The invention may be best understood with reference to the accompanying drawings wherein illustrative embodiments are shown.

BRIEF DESCRIPTION OF THE DRAWINGS

FIG. 1 is a side elevation view partially in section of the hemostatic device provided in accordance with the first embodiment of the present invention;

FIG. 2 is an enlarged front elevational view of a screw plug provided in accordance with the first embodiment of the present invention;

FIG. 5 is a side elevational view in partial section of the hemostatic device provided in accordance with the first embodiment of the present invention, shown delivering the screw plug so as to be in blocking relation with a puncture in the vessel;

FIG. 6 is a side elevational view in partial section of the arterial wall with the screw plug provided in accordance with the first embodiment of the present invention, shown in a position producing closure and hemostasis of the percutaneous puncture site;

FIG. 7 is a side elevational view in partial section of a catheter device provided in accordance with a second embodiment of the present invention;

FIG. 8 is cross-sectional view of the catheter device provided in accordance with a second embodiment of the present invention taken along the line 8—8 of FIG. 7;

DETAILED DESCRIPTION OF THE PRESENTLY PREFERRED EXEMPLARY EMBODIMENTS

Figure 3:
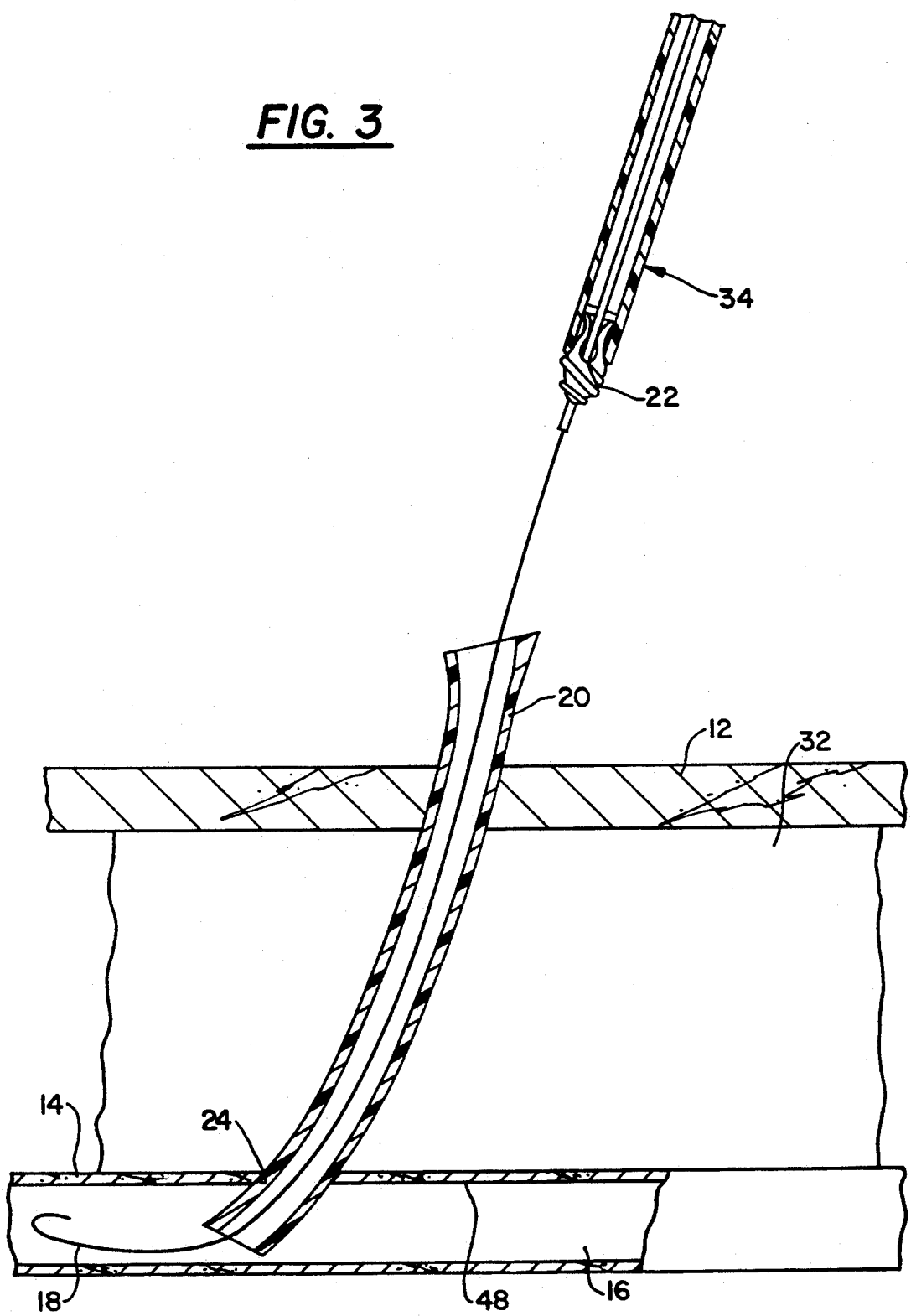
FIG. 3 is a side elevational view in partial section of a portion of the hemostatic device constructed in accordance with the first embodiment of the invention, about to be inserted into a conventional arterial sheath extending through a percutaneous puncture into the arterial lumen.

Referring now in to the drawings, a device, generally indicated at 10, is shown in FIG. 1, which embodies the principles of the present invention. The device 10 may be utilized for effecting hemostasis and closure of a puncture or other openings in a blood vessel, duct or lumen in a living being. This device has particular utility when used in connection with intravascular procedures such as angiography, balloon angioplasty, intra-aortic balloon pumping and other types of percutaneous intravascular or intracardiac interventions. A brief description of a conventional percutaneous transcatheter cardiovascular procedure e.g., coronary angiography, percutaneous transluminal angioplasty, is given with reference to FIG. 3, to best appreciate the features of the present invention.

In such a conventional procedure, an angiographic needle such as a Seldinger or Argon needle (not shown) is inserted percutaneously through the skin 12, into an artery, such as the femoral artery 14. The angiographic needle with its tip disposed within the arterial lumen 16 is held while the flexible end of an angiographic guide wire 18 is advanced through the needle into the arterial lumen 16. Once the guide wire is felt to be easily movable within the arterial lumen, the angiographic needle is withdrawn leaving the guide wire in place. A conventional arterial sheath 20 and arterial dilator (not shown) are threaded over the proximal end of the guide wire 18 and advanced over the guide wire through the skin and arterial wall into the arterial lumen 16. The guide wire and dilator are then removed leaving the arterial sheath in place. Angiographic catheters or other intraluminal devices (not shown) are then passed through the arterial sheath 20 and advanced within the artery to the target site by passage over the guide wire. Once the angiographic or angioplasty procedure is completed, the catheters and guide wires are removed, leaving the arterial sheath in place. Finally, the arterial sheath is removed, which then, conventionally requires the physician or other trained medical personnel to apply manual pressure to the puncture site until hemostasis has been achieved.

The device 10 and method of the present invention produce hemostasis and closure of arterial puncture sites by percutaneous means, without necessitating prolonged manual arterial compression.

In accordance with a first embodiment of the invention, hemostasis is effected by placing a screw-like plug, generally indicated at 22, into the puncture orifice 24. This screw-plug 22 is shown in FIG. 2 and consists of a body 26 made of hemostatic, thrombogenic, bio-absorbable material which is firm yet compressible to allow passage though the arterial sheath 20 and resilient to allow the screw-plug to return its natural shape once passed through the sheath 20. The distal end of the body is tapered to facilitate ease of entry into the puncture orifice 24. The body 26 of the screw-plug 22 is compact and rapidly flares outward in its proximal portion to maximally occlude the puncture site while minimizing protrusion of the plug into the arterial lumen 16. Screw-like threads 28 are disposed on the outer periphery of the body 26 so that with a turning motion directed into the puncture orifice 24, the screw-plug 22 advances into the puncture orifice engaging the threads 28 with the surrounding walls, thereby preventing dislodgement of the screw-plug due to the force of pulsatile blood flow. As an alternative to providing threads 28, the body 26 may include any means for engaging a vessel wall, such a jagged periphery, or the inclusion of protrusions or the like. The proximal end of the body includes wing members 30 which are shaped to embed within the subcutaneous tissue layer 32 and act to further stabilize the screw-plug 22 within the puncture orifice 24. The wing members 40 fold together so to fit into, and be held by, the firm yet flexible distal end of the delivery catheter, generally indicated at 34. The screw-plug 22 has a self-sealing orifice 36 which allows passage of a thin hollow tube 38, housing the guide wire 18, to pass therethrough. The orifice 36 closes when tube 38 and wire 18 are withdrawn.

The screw-plug 22 is delivered to the puncture site on the distal end of a delivery catheter 34, which is shown in FIG. 1. The delivery catheter 34 comprises a hollow tubular body 40 having a push member 42 disposed therein. In the illustrated embodiment, the push member is of a generally cylindrical configuration which extends the length of the delivery catheter 34. The push member 42 includes a thumb handle 44 on proximal end 46. Both the tubular body 40 and the push member are constructed of firm yet flexible material such as PET, polyvinyl chloride or the like. In the illustrated embodiment, the outer diameter of the tubular body is 8 French or less, which enables the tubular body to easily pass through the arterial sheath 20. End 47 of the tubular member 40 includes a flange portion 49. The flange portion 49 may be gripped with one's fingers when driving the push member forward, which will become more apparent below.

The screw-plug 22 is disposed at the distal end of the delivery catheter 34 upon folding the flexible wings together and inserting the screw-plug through opening 51, as shown in FIG. 1.

The thin, removable hollow tube 38 traverses the entire length of the push member 42 and is aligned with the self-sealing orifice 36 of the screw-plug. The hollow tube 38 houses the guide wire 18, and is disposed through the entire length of the device 10. Since blood is carried up into the tube 38 by a combination of capillary action and pulsatile blood flow, the tube 18 also serves to indicate when the tip of the screw-plug 22 has entered the arterial puncture site 24. A filament (not shown) may be connected to the body 26 of the screw-plug 22 which functions to retrieve the screw-plug 22 if a faulty placement thereof should occur.

Thus, once the catheterization or intravascular procedure is completed, and preferably with the sheath 20 remaining in place, the guide wire 18 is re-advanced through the arterial sheath 20 into the arterial lumen 16. As shown in FIG. 3, the screw-plug 22 being disposed at the distal end of the delivery catheter 34 is threaded over the guide wire 18. The guide wire 18 guides the screw-plug 22 into the puncture orifice as the delivery catheter 34 is advanced.

Figure 4:
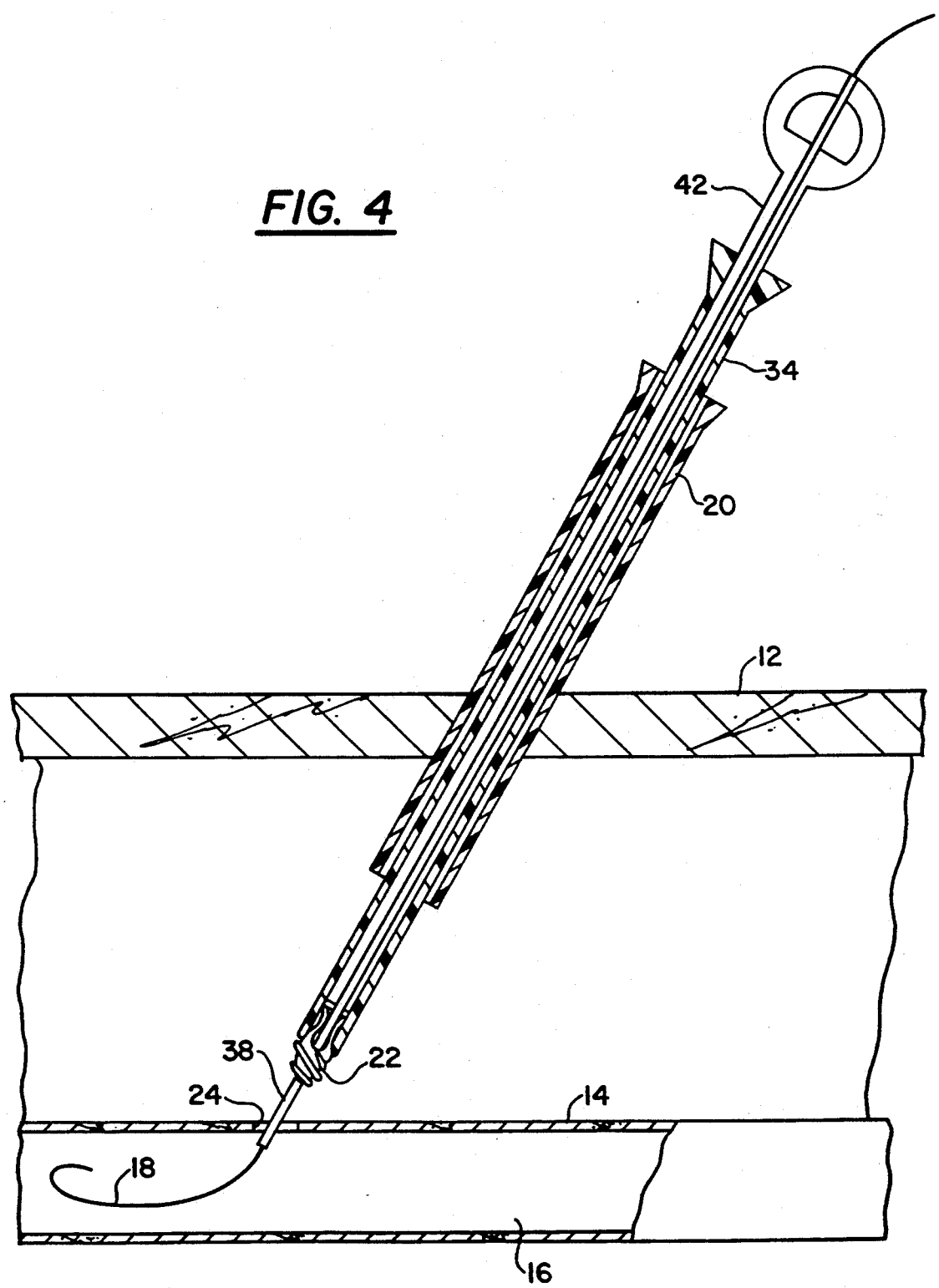
FIG. 4 side elevational view in partial section of the hemostatic device provided in accordance with the first embodiment of the present invention, shown delivering a screw plug to the arterial puncture site over a guide wire, as the arterial sheath is removed.

As shown in FIG. 4, the arterial sheath 20 is retracted from the arterial lumen 16 as the device 10 is advanced over the guide wire 18 and through the sheath 20 until the device 10 approaches the puncture orifice 24. Brief manual compression of the artery 14 may be used to stop blood flow during retraction of the arterial sheath 20 and until the screw-plug 22 is seated within the puncture orifice 24.

FIG. 5 shows the tip of the screw-plug 22 in contact with the puncture orifice 24. As previously described, when in contact with the puncture orifice 24, blood will be visualized within the thin hollow tube 38 due to capillary action and the pressure of pulsatile blood flow. The delivery catheter 34 ma be then rotated and further advanced to position the screw-plug 22 within the puncture orifice 24. With proper seating of the screw-plug 22, manual pressure on the artery 14 is released, the guide wire 18 and hollow tube 38 are withdrawn from the artery and from the delivery catheter 34. When hemostasis is confirmed, the push member 40 is advanced to expel the screw-plug 22 from the delivery catheter 34. Finally, the delivery catheter 34 and the arterial sheath are withdrawn from the tissue.

It is preferable to retract the arterial sheath 20 from the puncture without completely removing it from the patient's body prior to threading the delivery catheter 34 over the guide wire 18, since the sheath 20 provides an unobstructed delivery channel for the delivery catheter 34 to pass therethrough to reach the puncture site. However, it can be appreciated that arterial sheath can be completely removed from the body. The guide wire 18 can then be reintroduced into the puncture site prior to removing the final catheter required for the procedure. The final catheter may then be removed. With the guide wire in place, the delivery catheter may then be threaded thereon and moved to place the screw-plug into blocking relation with the puncture site.

FIG. 6 shows the deployed screw-plug 22 producing hemostatic closure of puncture orifice 24. The screw threads 28 are firmly engaged with the surrounding arterial wall 48. Once deployed, the wing members 30 spring outward to embed within the subcutaneous tissue 32 to render additional support for the screw-plug 22.

A second embodiment of the device 10 is shown in FIG. 7. The device 10 is similar in many respects to that of the first embodiment. Accordingly, corresponding part numbers are assigned the same reference numbers and will not be specifically described.

In this embodiment, the device 10 comprises a hemostatic catheter, generally indicated at 50, having an end portion 52 with a concave distal tip 53. The distal tip is shaped to exert direct mechanical pressure against the vessel puncture site 54. In the preferred embodiment, disposed at the end of the distal tip 53 is a plug member 56. The plug member 56 is of generally cylindrical configuration and is sized to conform to the distal tip 53. The plug member 56 is preferably composed of hemostatic, thrombogenic, bioabsorbable material. In the illustrated embodiment, the hemostatic catheter 50 comprises a hollow elongate body 58 made of a firm, yet flexible material such as PET, polyvinyl chloride or the like. The body 58 has a outer diameter of 8 French or less, to facilitate easy passage through the arterial sheath 20. Proximal to the distal tip 53 is a low pressure balloon 60. The balloon 60 is affixed to the body 58 by threads or the like. The balloon 60 is made of material similar to that of the elongate body 58, which may be inflated into a wedge shape with its widest base facing the distal end of the catheter 50. Alternatively, the balloon may be inflated into a corrugated shape or the like. The inflated balloon 60 serves to exert lateral pressure against the surrounding subcutaneous tissue 32 and by so doing, secures the distal tip 53 and the plug member 56 against the puncture site to provide direct mechanical hemostasis, which will become more apparent below.

The device 10 also includes a thin, removable hollow tube 38 that passes from the distal catheter tip and runs the length of the catheter, which, as in the first embodiment, serves the dual purpose of allowing the guide wire 18 to pass therethrough and to indicate proper positioning of the distal tip 53 relative to the artery 14, as indicated by the presence of blood within its lumen 16, as previously described. A passage 62 extending the longitudinal axis of the body 58 is provided for inflating the balloon 60. The passage 62 connects with tube 64, which in turn is attached to inflating syringe 66. A stopcock 68 is provided to regulate the inflation of the balloon 60. The plug member 56 has a self-sealing orifice 70 which closes upon removal of the hollow tube 38 and guide wire 18, thus, preventing backflow of blood into the catheter 50 during mechanical hemostasis.

If desired, a high viscosity bio-absorbable hemostatic gel 57 or glue may be applied to the plug member 56 to aid in sealing the puncture site 54 and orifice 70 during hemostasis.

Figure 9:
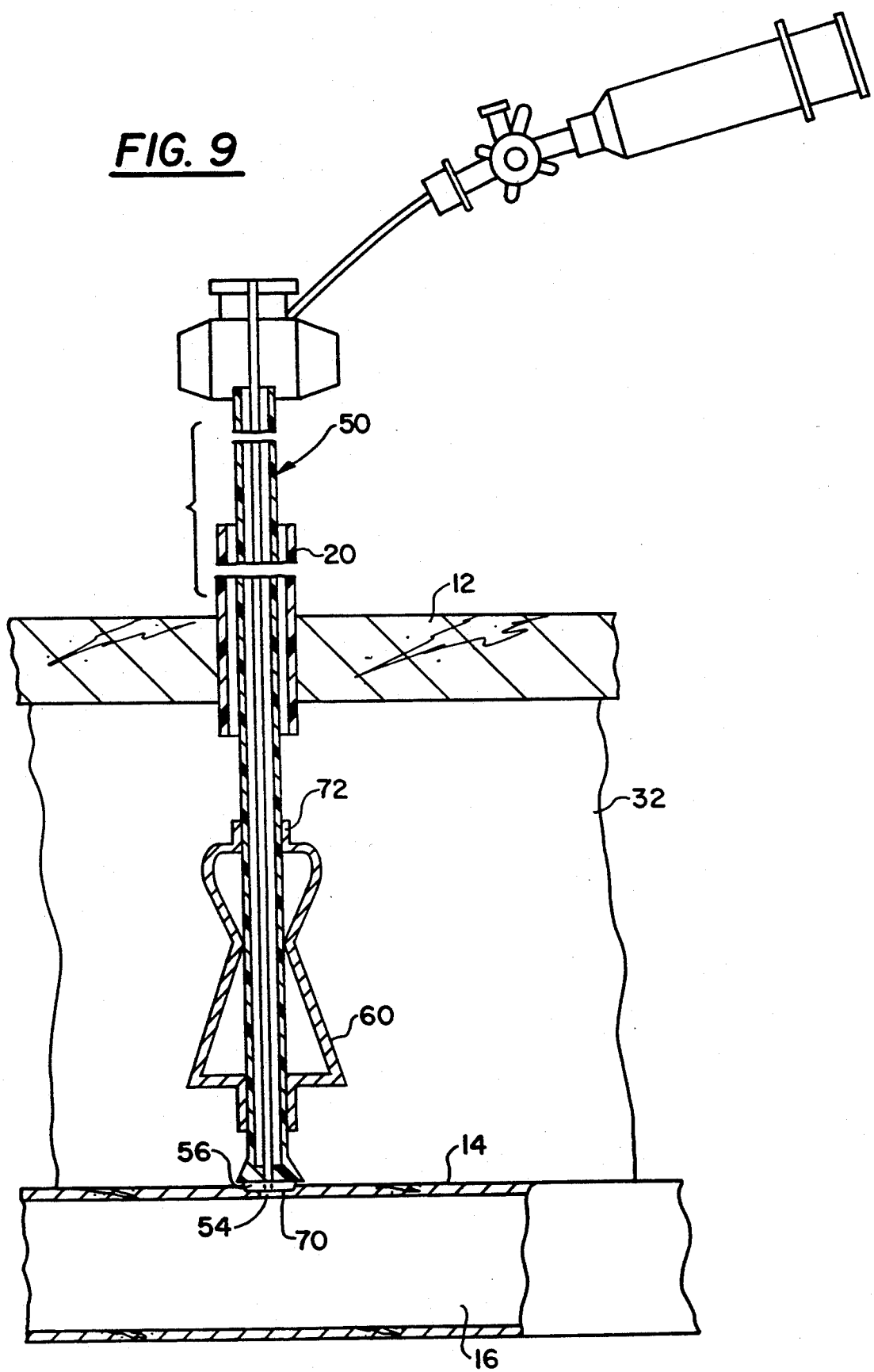
FIG. 9 is a side elevational view in partial section of the catheter device of a second embodiment of the present invention, shown in position to produce hemostasis and closure of the puncture site with the guide wire removed.

With reference to FIG. 9, the procedure for placing the plug member 56 in blocking relation with the puncture site 54 will be appreciated. Upon completion of the catheterization procedure following removal of the catheters required therefor, and with the arterial sheath 20 remaining in place, the guide wire 18 is passed through the arterial sheath 20 into the arterial lumen 16. The hemostatic catheter 50 is threaded onto the proximal end of the guide wire 18 and is then advanced into the arterial sheath 20. Brief manual pressure is exerted on the artery 14 as the arterial sheath 20 is withdrawn from the arterial lumen 16, while the hemostatic catheter 50 is advanced until the plug member 56 is disposed against the arterial wall 48. The proper position of the device 10 relative to the arterial puncture site 54 is indicated by the presence of blood within the thin hollow tube 38. The balloon 60 is then inflated using the inflation syringe 66. Thereafter, the manual pressure on the artery 14 is released. The guide wire 18 is then withdrawn from the artery 14 and from the hemostatic catheter 50 respectively. The device 10 maintains mechanical hemostatic pressure directly to the arterial puncture site 54, without the need for prolonged manual arterial compression. The time required to complete hemostasis depends on whether or not a hemostatic gel 57 or glue had been applied to the plug member 56 prior to its insertion. FIG. 9 shows the hemostatic catheter 50 in place after removal of the guide wire 18, with the plug member 56 hemostatically occluding the arterial puncture site 54. The inflated balloon 60 stabilizes the plug member 56 against the puncture site 54 and will permit full patient ambulation while the catheter remains in place. Once hemostasis is achieved, the balloon is deflated and the hemostatic catheter and arterial sheath are removed from the patient.

Again, it is preferable to partially retract the arterial sheath 20 from the puncture without completely removing the sheath from the patient prior to threading the hemostatic catheter 50 onto the guide wire. However, the sheath may be completely withdrawn from the patient prior to threading the catheter 50 onto the guide wire, as described with reference to the first embodiment.

While it is preferable to utilize a separate member 56 with the hemostatic catheter 50, it can be appreciated that the distal tip 53 may include a plug member affixed thereto. Thus, the distal tip 53 may be directly placed into blocking relation with the puncture site to maintain mechanical hemostatic pressure thereon, without leaving a plug at the puncture site upon withdrawing the catheter 50.

The hemostatic balloon catheter device 10 may also seal vascular puncture sites by deploying thermoplastic-like sealant material using the combination of heat and pressure, preferably followed by rapid cooling. The combination of heat and pressure has been shown to be effective in fusing vascular tissues together.

Figure 10:
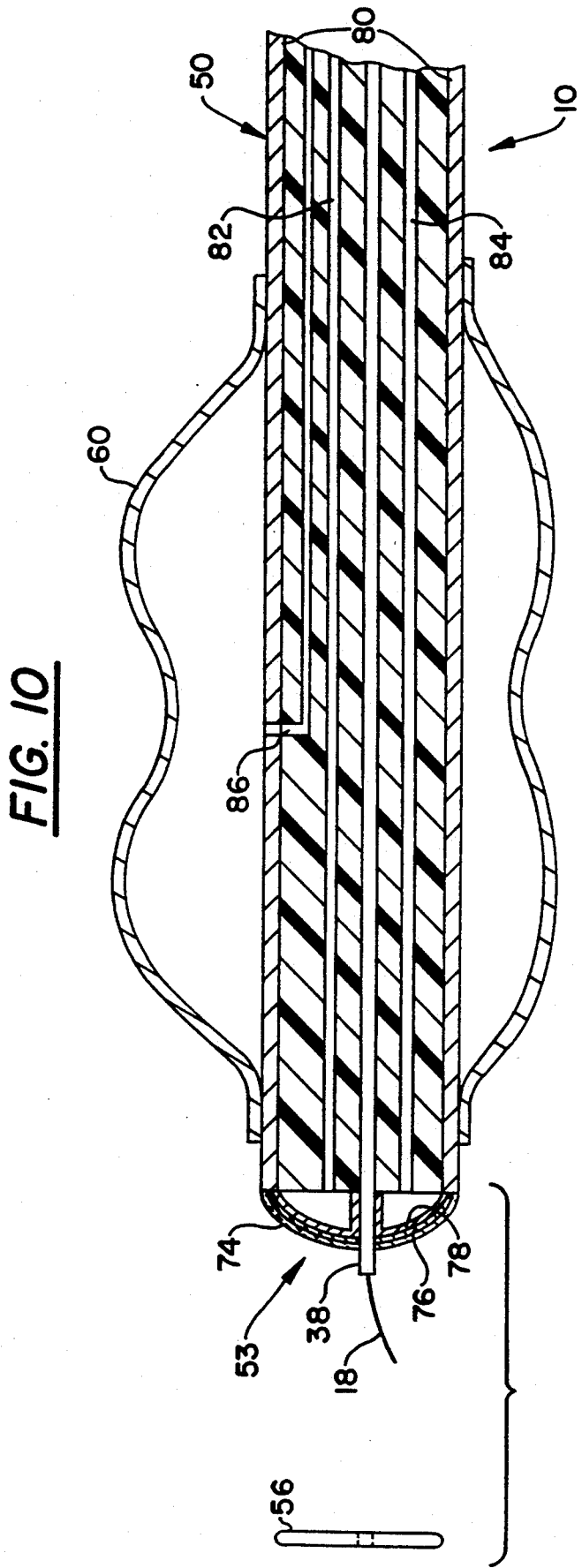
FIG. 10 is an enlarged partial sectional view of an end portion of the catheter device of the second embodiment including a heating element disposed in the distal end thereof.

Thus, the hemostatic catheter 50, shown in FIG. 10, is modified to include an element for heating the distal end thereof. The distal tip 53 preferably includes an outer teflon layer 74, a mid-layer 76 of stainless steel and an inner conductive layer 78, made of copper or other conductive materials. The conductive layer 78 is electrically connected to wires 80. The conductive layer 78 can be heated by a passing energy through the wires 80 from a variety of energy sources, such as AC, DC, RF, or microwave energy. Two infusion channels 82, 84 extend the length of the catheter body to allow for passage of coolant to and from the distal tip 53, which acts to quickly cool the tip 53 of the catheter 50. The catheter 50 includes a channel 86 for inflating the balloon 60.

Various plug members 56 may be delivered on the tip 53 of the catheter at room temperature in solid, disc-like form. The plug member 56 may be heat softened using heat generated by the conductive layer 78 and fused to the arterial puncture site 54 to block the puncture. Preferably, the plug material is then quickly cooled so as to minimize patient discomfort by passing coolant through channels 82, 84, however, cooling is not necessary to fuse the plug member to the puncture site. In the illustrated embodiment, the plug member is made of materials which may include bioabsorbable thermoplastic substances or tissue components consisting of collagen, blood products, subcutaneous tissues, or a combination thereof. It is preferable that the tissue components be supplied by the patient. Bioabsorbable thermoplastic substances, collagen, or tissue proteins are rendered softer and moldable by the combination of heat and pressure and subsequently may be hardened by rapid cooling while pressure is still exerted at the puncture site provided by the inflated balloon 60 on the catheter body 50.

It can be appreciated that the method of the present invention provides hemostatic closure of a puncture or other opening in other types of ducts or lumens within the body without obstructing blood flow.

Thus, it is to be understood that while the description of the invention as contained herein is directed to closing off percutaneous punctures in arteries, the device and method have wide-spread applications. It can be appreciated by those skilled in the art, that while the invention may have primary utility for the percutaneous hemostatic closure of arterial punctures following percutaneous transluminal intravascular procedures, the invention also facilitates percutaneous closure of punctures or openings in any organ, wall or tissue plane separating separate lumens or cavities in a living being.

It has thus been seen that the objects of this invention have been fully and effectively accomplished. It will be realized, however, that the foregoing preferred embodiments have been shown and described for the purposes of illustrating the structural and functional principles of the present invention, as well as illustrating the method of employing the preferred embodiments and are subject to change without departing from such principles. Therefore, this invention includes all modifications encompassed within the spirit of the following claims.

I claim:

1. A method of closing a puncture in a wall of an artery made for the purpose of moving an elongated cardiac catheter into the artery in which an exterior guide tube is extended through a passage leading to the puncture and through the puncture in the wall of the artery and into the artery so as to enable the catheter to be guidingly moved through the guide tube and into the artery, the method comprising the steps of:

withdrawing the cardiac catheter from the guide tube, extending a plug having a removable guide wire extending longitudinally therethrough into said guide tube so that the guide wire extends from the plug through said puncture, moving the guide tube outwardly so that it no longer extends within the puncture and leaves the guide wire extending through the puncture, moving the plug inwardly along the guide wire into blocking relation with said puncture, and withdrawing the guide wire from the plug so as to leave the plug sealed in blocking relation with said puncture.

2. The method as claimed in claim 1, further comprising providing said plug with means for engaging a wall of said artery, said engaging means retaining said plug in said puncture of the artery without substantially occluding blood flow in said artery.

3. The method as claimed in claim 2, further comprising providing said plug of hemostatic, thrombogenic, bio-absorbable material.

4. The method as claimed in claim 2, wherein a proximal portion of said plug is in a compacted, biased condition as the plug is moved into blocking relation with the puncture, said proximal portion expanding to an unbiased condition when said plug is sealed in blocking relation with the puncture.

5. The method as claimed in claim 2, wherein said engaging means is disposed at a distal portion of said plug, said engaging means including screw threads disposed about the periphery of said distal portion.

6. The method as claimed in claim 1, further comprising the step of inflating a balloon after moving the plug inwardly along the guide wire into blocking relation with said puncture, said balloon exerting lateral pressure against subcutaneous tissue so as to hold said plug in a sealed, blocking relation with said puncture.

7. The method as claimed in claim 6, further comprising the steps of:
heating said plug so as to fuse said plug to the arterial wall while said balloon is inflated.

8. The method as claimed in claim 6, further including providing a hemostatic, bio-absorbable gel on said plug.

9. The method as claimed in claim 7, wherein said plug is one of bioabsorbable, thermoplastic, and tissue components.

10. The method as claimed in claim 9, wherein said tissue components include collagen, blood and blood protein subcutaneous tissue.

11. A device for closing a puncture in a wall of an artery comprising:
an elongated member having a distal end, said elongated member sized to be fitted through a passageway leading to said puncture so that said distal end is disposed near said puncture in said artery,
separable plug means for plugging said puncture being disposed at said distal end of said elongated member,
movable guide means extending longitudinally through said elongated member and said plug means for extension through said puncture for guiding said plug means to said puncture, and
means for ejecting said plug means from said distal end of said elongated member so as to place said plug means in blocking relation with said puncture, a portion of said plug means engaging a wall of said artery when disposed in said blocking relation so as to seal said puncture.

12. A device as claimed in claim 11, wherein said movable guide means is a guide wire.

13. A device as claimed in claim 11, further including a guide tube, said guide tube being extended through an adjacent skin area through the body containing the artery, through the puncture in the wall of the artery and into the artery enabling a cardiac catheter to be guidingly moved through said guide tube and into the artery, said guide tube and cardiac catheter being removed from the puncture prior to placing said plug means into blocking relation with said puncture.

14. A device as claimed in claim 11, wherein said plug means includes a proximal portion and a distal portion, said proximal portion including expandable members which are in a compacted, biased condition while said plug means is disposed at said distal end of said elongated member, said expandable members expanding outwardly to an unbiased condition after being ejected therefrom, said distal portion including means for engaging a wall of said artery so as to retain said plug means in blocking relation with said puncture.

15. A device as claimed in claim 14, wherein said engaging means includes screw threads disposed about a periphery of said distal portion.

16. A device as claimed in claim 11, wherein said plug means is comprised of hemostatic, thrombogenic, bio-absorbable material.

17. A device as claimed in claim 11, wherein said elongated member is a tubular member having a longitudinal axis and wherein said ejecting means is a pusher element being movable along said longitudinal axis for expelling said plug means.

18. A device as claimed in claim 17, wherein said pusher element includes means for engaging a person's thumb, and wherein said tubular member includes means for engaging a person's fingers so that said pusher element may be moved along said longitudinal axis.

19. A device as claimed in claim 17, further comprising a thin, flexible tube disposed within said pusher element, said guide means being disposed within said flexible tube, said flexible tube being utilized for locating of said plug means within said puncture, said plug means being in proper location within said puncture when blood is present within said flexible tube.

20. A device as claimed in claim 11, wherein said plug means includes an orifice therethrough, said guide means being disposed through said orifice, said orifice automatically closing when said guide means is removed therefrom.

21. A device for closing a puncture in a wall of an artery comprising:
an elongated member including a distal end having plug means thereon, said elongated member sized to be fitted through a passageway leading to said puncture so that said distal end is disposed near the puncture in said artery,
movable guide means extending longitudinally through said elongated member and said plug means for extension through said puncture for guiding said plug means to said puncture, and
means for exerting pressure on subcutaneous tissue near said passageway so as to stably hold said plug means against said puncture.

22. A device as claimed in claim 21, wherein said exerting means comprises an inflatable balloon disposed about a lower peripheral portion of said elongated member, said balloon being inflated so as to stably hold said plug means against said puncture.

23. A device as claimed in claim 22, wherein said elongated member further includes means for inflating said balloon.

24. A device as claimed in claim 21, wherein said plug means is plug member being separable from said distal end and having an orifice therethrough, said guide means being disposed through said orifice, said orifice automatically closing when said guide means is removed therefrom.

25. A device as claimed in claim 24, wherein said plug member is formed from hemostatic, thrombogenic, bio-absorbable material.

26. A device as claimed in claim 21, wherein said plug means is affixed to said distal end of said elongated member.

27. A method of closing a puncture in a wall of an artery comprising the steps of:
extending a plug having a removable guide wire extending longitudinally therethrough into a passageway leading to the puncture so that the guide wire extends from the plug through said puncture,
moving the plug inwardly along the guide wire into blocking relation with said puncture, withdrawing the guide wire from the plug so as to leave the plug in blocking relation with said puncture; and heating said plug while pressure is exerted on said plug to fuse said plug to vascular tissue of the artery so as to seal said puncture.

28. The method as claimed in claim 27, wherein the step of heating said plug is followed by a step of rapidly cooling said plug.

29. The method as claimed in claim 27, wherein said plug is one of bioabsorbable, thermoplastic, and tissue components.

30. The method as claimed in claim 29, wherein said tissue components include collagen, blood and blood protein subcutaneous tissue.

31. A device for closing a puncture in a wall of an artery comprising:

an elongated member having a distal end, said elongated member sized to be fitted through a passageway leading to the puncture so that said distal end is disposed near the puncture in said artery, plug means for plugging said puncture being adjacent to said distal end of said elongated member, movable guide means extending longitudinally through said elongated member and said plug means and through said puncture for guiding said plug means to said puncture, means for exerting pressure on subcutaneous tissue near said passageway so as to stably hold said plug means against said puncture, and means for heating said plug means while said plug means is held against said puncture.

32. A device as claimed in claim 31, wherein said heating means includes a conductive layer disposed within said distal end.

33. A device as claimed in claim 31, further comprising means for cooling said plug means while said plug means is held against said puncture.

34. A device as claimed in claim 33, wherein said cooling means includes channels disposed adjacent said distal tip, a coolant flowing within said channels.

35. The device as claimed in claim 29, wherein said plug means is composed of one of bioabsorbable, thermoplastic, and tissue components.

36. The device as claimed in claim 35, wherein said tissue components include collagen, blood and blood protein subcutaneous tissue.

37. A method of closing a puncture in a wall of an artery comprising the steps of:

inserting a removable guide wire through said puncture into the artery;

threading a plug over said guide wire so that the guide wire extends from the plug through said puncture, moving the plug inwardly along the guide wire into blocking relation with said puncture, and withdrawing the guide wire from the plug so as to leave the plug sealed in blocking relation with said puncture.

38. A device for closing a puncture in a wall of an artery comprising:

an elongated member having a distal end, said elongated member sized to be fitted through a passageway leading to said puncture so that said distal end is disposed near said puncture in said artery, a separable plug member for plugging said puncture being disposed at said distal end of said elongated member, a movable guide element extending longitudinally through said elongated member and said plug member for extension through said puncture for guiding said plug member to said puncture, and an ejecting mechanism for ejecting said plug member from said distal end of said elongated member so as to place said plug member in blocking relation with said puncture, a portion of said plug member engaging a wall of said artery when disposed in said blocking relation so as to seal said puncture.

39. A device for closing a puncture in a wall of an artery comprising:

an elongated member including a distal end having a plug element thereon, said elongated member sized to be fitted through a passageway leading to said puncture so that said distal end is disposed near the puncture in said artery, a movable guide element extending longitudinally through said elongated member and said plug element for extension through said puncture for guiding said plug element to said puncture, and a pressure exerting mechanism for exerting pressure on subcutaneous tissue near said passageway so as to stably hold said plug element against said puncture.

40. A device for closing a puncture in a wall of an artery comprising:

an elongated member having a distal end, said elongated member sized to be fitted through a passageway leading to the puncture so that said distal end is disposed near the puncture in said artery, a plug member for plugging said puncture being adjacent to said distal end of said elongated member, a movable guide element extending longitudinally through said elongated member and said plug member and through said puncture for guiding said plug member to said puncture, a pressure exerting mechanism for exerting pressure on subcutaneous tissue near said passageway so as to stably hold said plug member against said puncture, and a heating element for heating said plug member while said plug member is held against said puncture.

41. A device for closing a puncture in a wall of an artery comprising:

an elongated member having a distal end, said elongated member sized to be fitted through a passageway leading to said puncture so that said distal end is disposed near said puncture in said artery, separable plug means for plugging said puncture being disposed at said distal end of said elongated member, said plug means including screw-threads disposed about a periphery of a distal portion thereof, movable guide means extending longitudinally through said elongated member and said plug means for extension through said puncture for guiding said plug means to said puncture, and means for ejecting said plug means from said distal end of said elongated member so as to place said plug means in blocking relation with said puncture, said screw-threads of said plug means engaging a wall of said artery when disposed in said blocking relation so as to seal said puncture.

42. A device as claimed in claim 40, wherein a proximal portion of said plug means includes expandable members which are in a compacted, biased condition while said plug means is disposed at said distal end of said elongated member, said expandable members expanding outwardly to an unbiased condition after being ejected therefrom.

43. A device for closing a puncture in a wall of an artery comprising:
an elongated member having a distal end, said elongated member sized to be fitted through a passageway leading to said puncture so that said distal end is disposed near said puncture in said artery,
a separable plug member for plugging said puncture being disposed at said distal end of said elongated member, said plug member including screw-threads disposed about a periphery of a distal portion thereof,
a movable guide element extending longitudinally through said elongated member and said plug member for extension through said puncture for guiding said plug member to said puncture, and
an ejecting mechanism for ejecting said plug member from said distal end of said elongated member so as to place said plug member in blocking relation with said puncture, said screw-threads of said plug member engaging a wall of said artery when disposed in said blocking relation so as to seal said puncture.

* * * * *